United States Patent
Zhan et al.

(10) Patent No.: US 11,879,856 B2
(45) Date of Patent: *Jan. 23, 2024

(54) TWO-STEP MATERIAL DECOMPOSITION CALIBRATION METHOD FOR A FULL SIZE PHOTON COUNTING COMPUTED TOMOGRAPHY SYSTEM

(71) Applicant: CANON MEDICAL SYSTEMS CORPORATION, Otawara (JP)

(72) Inventors: Xiaohui Zhan, Vernon Hills, IL (US); Xiaofeng Niu, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 101 days.

This patent is subject to a terminal disclaimer.

(21) Appl. No.: 17/571,087

(22) Filed: Jan. 7, 2022

(65) Prior Publication Data

US 2022/0128488 A1    Apr. 28, 2022

Related U.S. Application Data

(62) Division of application No. 16/915,575, filed on Jun. 29, 2020, now Pat. No. 11,249,035.

(51) Int. Cl.
| | |
|---|---|
| *G01N 23/046* | (2018.01) |
| *A61B 6/03* | (2006.01) |
| *A61B 6/00* | (2006.01) |
| *G01N 23/083* | (2018.01) |

(52) U.S. Cl.
CPC ........... *G01N 23/046* (2013.01); *A61B 6/032* (2013.01); *A61B 6/4241* (2013.01); *A61B 6/582* (2013.01); *G01N 23/083* (2013.01); *G01N 2223/04* (2013.01); *G01N 2223/20* (2013.01); *G01N 2223/303* (2013.01); *G01N 2223/419* (2013.01); *G01N 2223/50* (2013.01)

(58) Field of Classification Search
CPC .............. G01N 23/046; G01N 23/083; G01N 2223/04; G01N 2223/20; G01N 2223/303; G01N 2223/419; G01N 2223/50; G01N 2223/423; A61B 6/032; A61B 6/4241; A61B 6/582
See application file for complete search history.

(56) References Cited

U.S. PATENT DOCUMENTS

| | | | |
|---|---|---|---|
| 11,249,035 B2 * | 2/2022 | Zhan | .............. G01N 23/046 |
| 2007/0076842 A1 | 4/2007 | Tkaczyk et al. | |
| 2016/0113603 A1 * | 4/2016 | Schirra | ................. A61B 6/032 250/252.1 |
| 2017/0224299 A1 | 8/2017 | Petschke et al. | |
| 2018/0252822 A1 | 9/2018 | Svensson et al. | |

OTHER PUBLICATIONS

Schmidt, Taly Gilat, et al, "A spectral CT method to directly estimate basis material maps from experimental photon-counting data", IEEE Trans Med Imaging. vol. 36 , Issue: 9, p. 1808-1819. https://ieeexplore.ieee.org/abstract/document/7906625.

* cited by examiner

*Primary Examiner* — Courtney D Thomas
(74) *Attorney, Agent, or Firm* — Oblon, McClelland, Maier & Neustadt, L.L.P.

(57) ABSTRACT

A method and a system for providing calibration for a photon counting detector forward model for material decomposition. The flux independent weighted bin response function is estimated using the expectation maximization method, and then used to estimate the pileup correction terms at each tube voltage setting for each detector pixel.

15 Claims, 5 Drawing Sheets

TWO-STEP MATERIAL DECOMPOSITION CALIBRATION METHOD FOR A FULL SIZE PHOTON COUNTING COMPUTED TOMOGRAPHY SYSTEM

CROSS-REFERENCE TO RELATED APPLICATION(S)

This application is a division application of U.S. application Ser. No. 16/915,575, filed Jun. 29, 2020, the entire contents of which are incorporated herein by reference.

BACKGROUND

Technical Field

The disclosure relates to material decomposition in a full size photon counting computed tomography system.

Description of the Related Art

Computed tomography (CT) systems and methods are typically used for medical imaging and diagnosis. CT systems generally create projection images through a subject's body at a series of projection angles. A radiation source, such as an X-ray tube, irradiates the body of a subject and projection images are generated at different angles. Images of the subject's body can be reconstructed from the projection images.

Conventionally, energy-integrating detectors (EIDs) and/or photon-counting detectors (PCDs) have been used to measure CT projection data. PCDs offer many advantages including their capacity for performing spectral CT, wherein the PCDs resolve the counts of incident X-rays into spectral components referred to as energy bins, such that collectively the energy bins span the energy spectrum of the X-ray beam. Unlike non-spectral CT, spectral CT generates information due to different materials exhibiting different X-ray attenuation as a function of the X-ray energy. These differences enable a decomposition of the spectrally resolved projection data into different material components, for example, the two material components of the material decomposition can be bone and water.

Even though PCDs have fast response times, at high X-ray flux rates indicative of clinical X-ray imaging, multiple X-ray detection events on a single detector may occur within the detector's time response, a phenomenon called pileup. Left uncorrected, pileup effect distorts the PCD energy response and can degrade reconstructed images from PCDs. When these effects are corrected, spectral CT has many advantages over conventional CT. Many clinical applications can benefit from spectral CT technology, including improved material differentiation since spectral CT extracts complete tissue characterization information from an imaged object.

One challenge for more effectively using semiconductor-based PCDs for spectral CT is performing the material decomposition of the projection data in a robust and efficient manner. For example, correction of pileup in the detection process can be imperfect, and these imperfections degrade the material components resulting from the material decomposition.

In a photon counting CT system, the semiconductor-based detector using direct conversion is designed to resolve the energy of the individual incoming photons and generate measurement of multiple energy bin counts for each integration period. However, due to the detection physics in such semiconductor materials (e.g. CdTe/CZT), the detector energy response is largely degraded/distorted by charge sharing, k-escape, and scattering effects in the energy deposition and charge induction process, as well as electronic noise in the associated front-end electronics. Due to finite signal induction time, at high count-rate conditions, pulse pile-up also distorts the energy response, as discussed above.

Due to sensor material non-uniformity and complexity of the integrated detection system, it is impossible to do accurate modeling of such detector response for a PCD just based on physics theories or Monte Carlo simulations with a certain modeling of the signal induction process, which modeling determines the accuracy of the forward model of each measurement. Also, due to uncertainties in the incident X-ray tube spectrum modeling, the modelling introduces additional errors in the forward model, and all these factors eventually degrade the material decomposition accuracy from the PCD measurements, therefore the generated spectral images.

Calibration methods have been proposed to solve similar problems in literature. The general idea is to use multiple transmission measurements of various known path lengths to modify the forward model such that it agrees with the calibration measurements. Some ideas are applied on estimation of the X-ray spectrum in conventional CT, see Sidky et al., Journal of Applied Physics 97(12), 124701 (2005) and Duan et al., Medical Physics 38(2), February, 2011, and later adopted on photon-counting detectors to estimate the combined system spectral response, see Dickmann et al., Proc. SPIE 10573, Medical Imaging 2018: Physics of Medical Imaging, 1057311 (Mar. 9, 2018). However, there can be many variations in the detail design and implementation of the calibration method, especially considering the application feasibility in a full 3rd generation CT geometry, which has not been demonstrated or documented in literature so far.

SUMMARY

The embodiments presented herein relate to a two-step calibration method for the PCD forward model for material decomposition. The method consists of two parts: 1) estimation of the flux independent weighted bin response function $S_{wb}$ (E) using the expectation maximization (EM) method, and 2) estimation of the pileup correction term $P_b(E, N_b, N_{tot})$. Once $S_{wb}$ (E) is estimated from the calibration at each tube voltage (kVp) setting for each detector pixel, it is saved as a software calibration table in the system. It is then used as an input to estimate the pileup correction terms $P_b(E, N_b, N_{tot})$ at higher flux scans. Both tables are then used for the material decomposition in operational scans to estimate the basis material path lengths. The calibration tables are updated from time to time based on the system/detector performance variations.

BRIEF DESCRIPTION OF THE DRAWINGS

The application will be better understood in light of the description which is given in a non-limiting manner, accompanied by the attached drawings in which.

DETAILED DESCRIPTION OF THE PREFERRED EMBODIMENTS

Reference throughout this specification to "one embodiment" or "an embodiment" means that a particular feature, structure, material, or characteristic described in connection with the embodiment is included in at least one embodiment of the application, but do not denote that they are present in every embodiment.

Thus, the appearances of the phrases "in one embodiment" or "in an embodiment" in various places throughout this specification are not necessarily referring to the same embodiment of the application. Furthermore, the particular features, structures, materials, or characteristics may be combined in any suitable manner in one or more embodiments.

Figure 1:
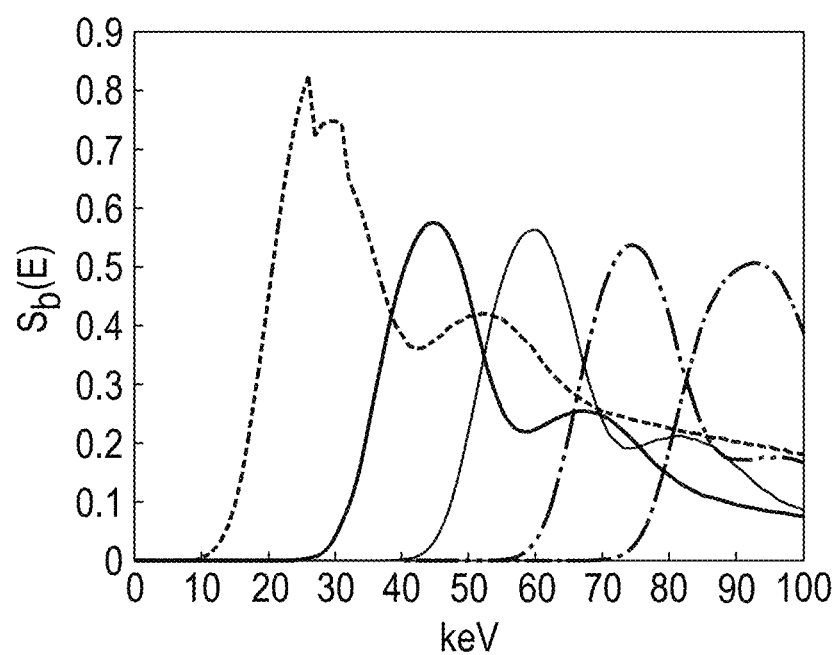
FIG. 1 shows an example of a PCD bin response function $S_b(E)$ for a photon counting detector. Each curve stands for an example function for each energy bin.

In a transmission measurement using a photon counting energy-resolving detector (PCD), the forward model can be formulated as below:

$$N_b(l_1, \ldots) = N_0 \times \int dE w(E) S_b(E) \exp(-\Sigma \mu_m l_m), \quad (1)$$

where $S_b(E)$ denotes the bin response function defined as $S_b(E) = \int_{E_{bL}}^{E_{bH}} R(E, E') dE'$ where $R(E,E)$ is the detector response function, and $E_{bL}$ and $E_{bH}$ are the low and high energy threshold of each counting bin. FIG. 1 shows an example model of a typical $S_b$ (E) function for a PCD, where a long tail above the energy window is induced by charge sharing, k-escape and scattering effect. The low energy tail is mostly due to the finite energy resolution from the associated electronic noise. $N_0$ is the total flux from an air scan, $\mu_m$ and $l_m$ are the $m^{th}$ basis material linear attenuation coefficient and path length. w(E) is the normalized incident X-ray spectrum. In practice, both w(E) and $S_b$ (E) are not exactly known, and they can be combined as one term, $S_{wb}$ (E)=w(E)$S_b$ (E), called thereafter the weighted bin response function. If $S_{wb}$ (E) can be calibrated through measurements, the decomposition problem at low flux condition can be well solved.

For a high flux scan condition (e.g. a few percent of pulse pileup), pulse pileup introduces additional spectral distortion in the measurement. One way to correct for the pileup effect is to introduce additional correction terms (e.g. see Dickmann above, who uses the measured count rate(s) as input). And this type of additional calibration is based on an accurate estimation of the flux independent weighted bin response $S_{wb}$ (E). How to estimate $S_{wb}$(E) in a full size 3rd generation CT system is a first problem solved in the present application.

At typical CT clinical scan conditions, it is common to encounter a few percent or higher pulse pileup for some measurements. The resulting effect in material decomposition depends on the measured spectrum as well as the flux. Without knowing the actual detector response, one can only do a limited number of transmission measurements to adjust the forward model. For a full CT system in clinical setting, it is crucial to have a feasible calibration procedure. Therefore, how to efficiently parameterize the model and optimize the calibration procedure is the second problem solved in the present application.

Additional practical challenges of conducting such a two-step calibration in a full size CT system include the following, and they have not been addressed or solved in prior arts, which are mostly targeted for small scale bench-top systems: fan-angle dependent weighted spectral response due to beam pre-filtration (e.g. bowtie filters); minimum flux limited due to the X-ray tube operational specifications and fixed system geometry; full detector ring calibration with various detector response across the pixels; limited space for in-system calibration phantom positioning; complication when calibrating on a rotating system with anti-scatter-grids; calibration systematic error and related mechanical design tolerances; non-ideal detectors with uniformity issue on energy resolution, counting, and drifts of the energy threshold settings, etc.

All the above non-ideal factors need to be considered for a photon counting CT to reach image qualities competitive to conventional energy integrating detector (EID)-based systems which have much simpler detector response modeling and related calibrations, while maintaining a similar calibration procedure/workflow that does not significantly increase the system down time.

In one non-limiting embodiment, a two-step calibration method for the PCD forward model for material decomposition is applied. The method consists of two parts: 1) estimation of the flux independent weighted bin response function $S_{wb}$ (E) using the expectation maximization (EM) method, and 2) estimation of the pileup correction term $P_b$(E, $N_b$, $N_{tot}$) which is a function of energy (E) and the measured bin counts ($N_b$, $N_{tot}$), where $N_b$ is the individual bin count and $N_{tot}$ is the total count of all the energy bins. The calibrated forward model can be expressed as:

$$N_b(l_1, \ldots, M) = N_0 \int^{Emax} dE S_{wb}(E) * P_b(E, N_b, N_{tot}) \exp(-\Sigma \mu_m l_m) \quad (2)$$

Here, instead of using only two materials, as in prior arts (e.g., see Dickmann), the method uses 2-5 different materials such as polypropylene, water, aluminium, titanium/copper, and k-edge materials to calibrate the weighted bin response function $S_{wb}$ (E) at low flux. With more selective materials used in the calibration, the number of total path lengths is reduced to achieve equivalent or better results.

Step 1: With an appropriate tube spectrum modelling to capture the characteristic peaks in the incident spectrum, and a physical model to simulate the photon-counting detector spectral response, an initial guess of $S_{wb}$ (E) can be produced. By using the EM method (e.g., see Sidky), $S_{wb}$ (E) can be reliably estimated for this very ill-conditioned problem based on a few transmission measurements.

Here, $P_b$(E, $N_b$, N tot) is assumed to be constant in Step 1. The calibrated forward model can be simplified to a system of linear equations $$N_b(l_1 \ldots M) = N_0 \int^{Emax} dE S_{wb}(E) \exp(-\Sigma \mu_m l_m) \quad (3)$$

Usually, the number of data measurements (M) is much smaller than the number of unknowns ($E_{max}$). With the assumption of Poisson distribution of the data acquisition, an iterative EM algorithm can be derived to find the optimal estimation of the unknown energy bin response function $S_{wb}$ (E), as described below.

When estimating the bin response function using low flux data acquisition, the pileup effect correction $P_b$ is assumed to be a known term (e.g. constant). So, the model is simplified to $$N_b = N_0 \int dE S_{wb}(E) [\exp[-\Sigma_m(E) l_m]] \quad (4)$$

Let $A^j(E)=\exp[-\Sigma\mu_m(E)l_m^j]$ represent the attenuated pathlength for j-th measurement. Thus, for each measurement j, we have $$N_b^j = N_0 \int dE S_{wb}(E) A^j(E) = N_0 \Sigma_E S_{wb}(E) A^j(E) \qquad (5)$$

With M measurements, the data acquisition can be written in the matrix form below $$N_0 \begin{pmatrix} A^1(1) & \cdots & A^1(E_{max}) \\ \vdots & \ddots & \vdots \\ A^M(1) & \cdots & A^M(E_{max}) \end{pmatrix}_{M \times E_{max}} \cdot \begin{pmatrix} S_{wb}(1) \\ \vdots \\ S_{wb}(E_{max}) \end{pmatrix}_{E_{max} \times 1} = \begin{pmatrix} N_b^1 \\ \vdots \\ N_b^M \end{pmatrix}_{M \times 1}$$

or $$A \cdot S_{wb} = N_b$$

By applying the EM iterative algorithm, the $S_{wb}$ can be estimated by $$S_{wb}^{(k+1)} = S_{wb}^{(k)} \odot ((A^T \cdot (N_b \oslash (A \cdot S_{wb}^{(k)}))) \oslash (A^T \cdot 1)) \qquad (6)$$

where
k: iteration number
•: matrix multiplication
⊙: element-wise multiplication
⊘: element-wise division
1: vector of ones with size of M×1
the updating formula for $S_{wb}(E)$ is given by $$S_{wb}^{(k+1)}(E) = S_{wb}^{(k)}(E) \frac{\sum_{j'} A^{j'}(E) \frac{N_b^{j'}}{\sum_{E'} A^{j'}(E') s_{wb}^{(k)}(E')}}{\sum_{j'} A^{j'}(E)} \qquad (7)$$

Step 2: Once $S_{wb}(E)$ is estimated from the calibration at each tube voltage (kVp) setting for each detector pixel, it is saved as a software calibration table on the system. It will be used as an input to further estimate the pileup correction terms $P_b$ (E, $N_b$, $N_{tot}$) at higher flux scans. Both tables are then used for the material decomposition in object/patient scans to estimate the basis material path lengths.

The calibration tables are updated from time to time based on the system/detector performance variations. This can also be designed as an iterative procedure. If the image quality is not good enough on a quality check phantom, this calibration process is repeated with the updated calibration tables from the last iteration as the initial guess.

Figure 2:
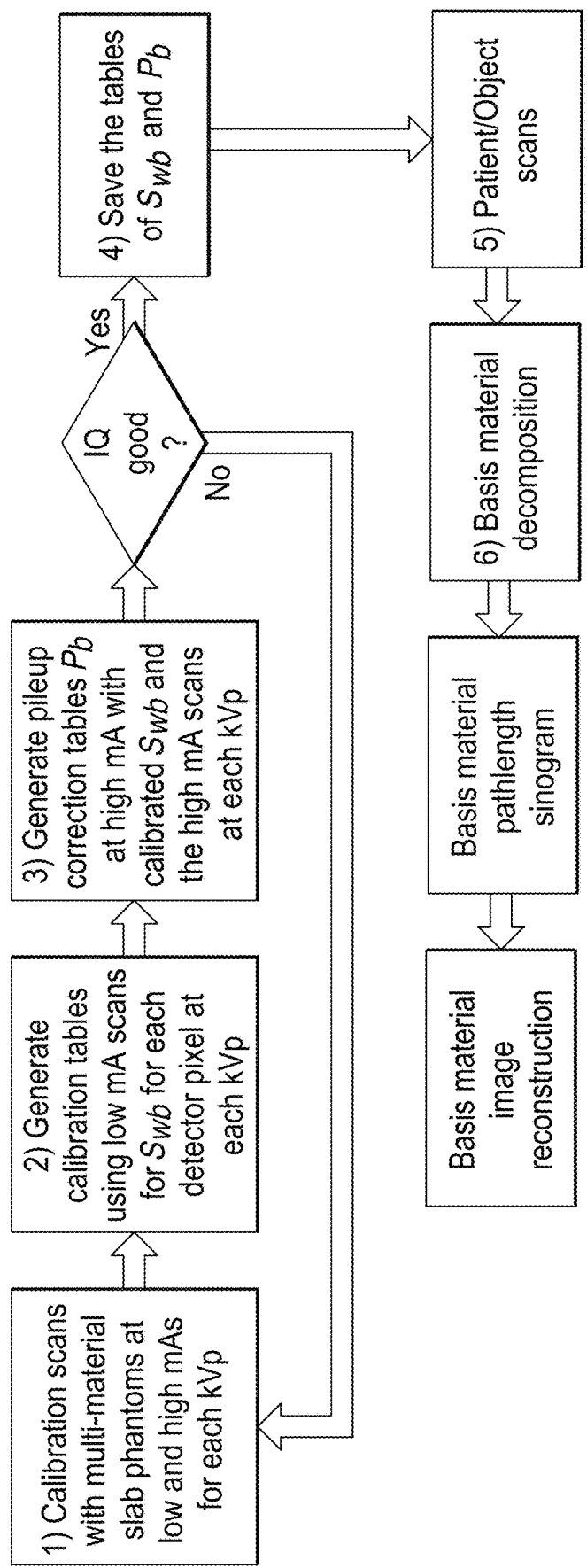
FIG. 2 shows a material decomposition calibration and processing workflow.

The high level workflow of the above process is demonstrated in FIG. 2. Steps 1) to 4) represent the calibration workflow, and steps 5) to 8) demonstrate how the calibration tables are used in the operational scans of patients/objects to produce spectral images.

First, a series of low flux scans on various material slabs are collected at each tube kVp setting, which is the peak potential applied on the X-ray tube. Typical CT systems support a few kVp settings from 70 to 140 kVp which generate different energy spectrums from the X-ray tube for different scan protocol. For a CT scan, both mA and kVp need to be pre-selected before the tube is turned on. Then, the low flux weighted bin response function $S_{wb}$ is estimated and with the estimated $S_{wb}$, the high flux slab scans are used to estimate the additional parameters in the pileup correction term $P_b$. With the estimation calibration tables of $S_{wb}$ and $P_b$ for each detector pixel, the quality of the calibration is checked on a quality phantom, e.g. a uniform water phantom, or phantom with multiple inserts with uniform known materials. The image quality is assessed with predefined standards, and if it is passed, the current calibration tables are saved and then used for the following patient/object scans data processing. Otherwise, the procedure goes through the first three steps again using the last iteration of $S_{wb}$ and $P_b$ as the initial guess. Here, commonly examined standards are: image CT number accuracy, uniformity, spatial resolution, noise and artifacts. To check the quality of this calibration, these metrics should all be checked, especially the accuracy and artifacts like ring or bands in the image, which indicate the calibration is not good enough.

Figure 3:
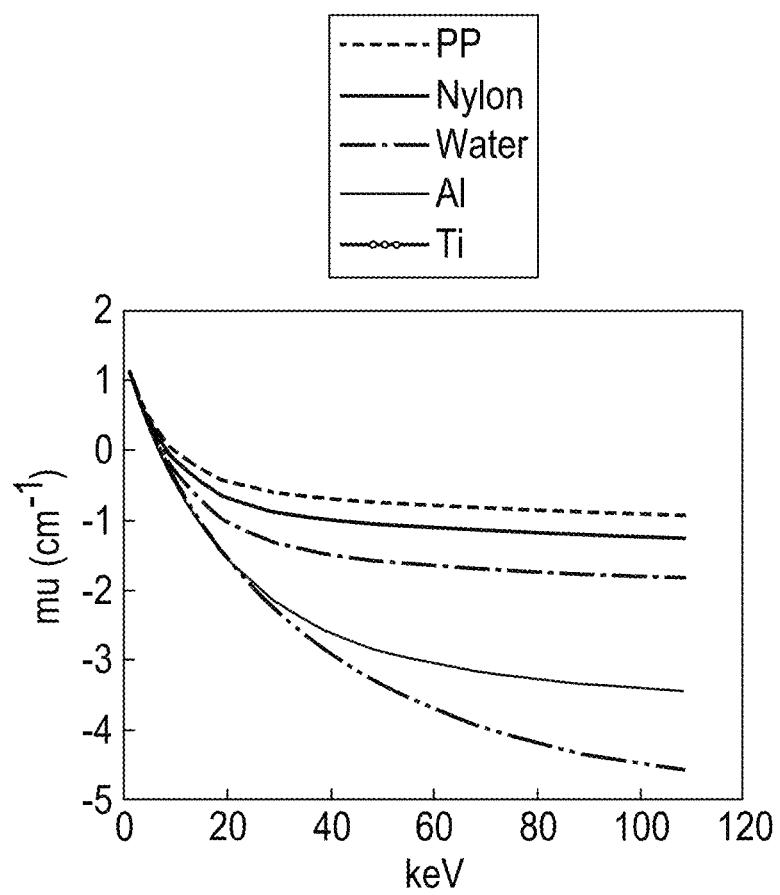
FIG. 3 shows normalized linear attenuation coefficients for different materials.

To choose the optimal materials and path lengths for this calibration, one can use the normalized linear attenuation coefficient vs. energy curves (FIG. 3) to choose the ones that are different from each other, e.g. polypropylene, water, aluminum, titanium can be a good group of combinations for such calibrations which covers a large range of common materials present in human body.

In order to satisfy the low flux condition through the calibration measurement to minimize the pileup effect in the flow diagram, step 1, one can select to use nτ<x, where x ∼0.005-0.01 and n is the pixel count rate with the lowest tube flux setting, and τ is the effective dead time of the PCD Application Specific Integrated Circuit (ASIC). By satisfying this condition, one can calculate the shortest path length of each selected calibration material, and the rest of path lengths can either be selected by equal spacing in path length or in resulting measurement count rate.

Figure 4:
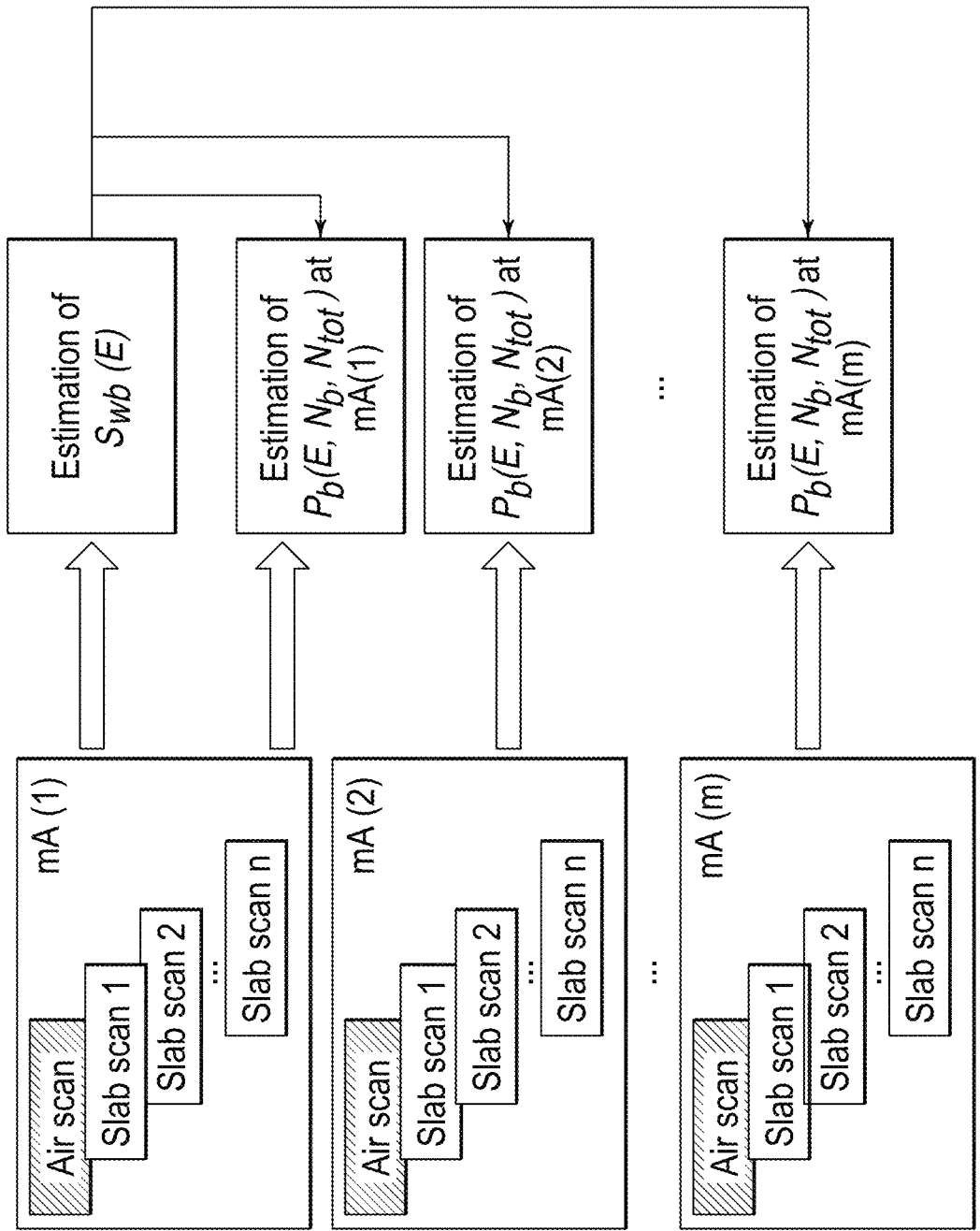
FIG. 4 shows a schematic of a calibration structure design, where the pileup correction tables $P_b$ are generated and used for each mA individually.
Figure 5:
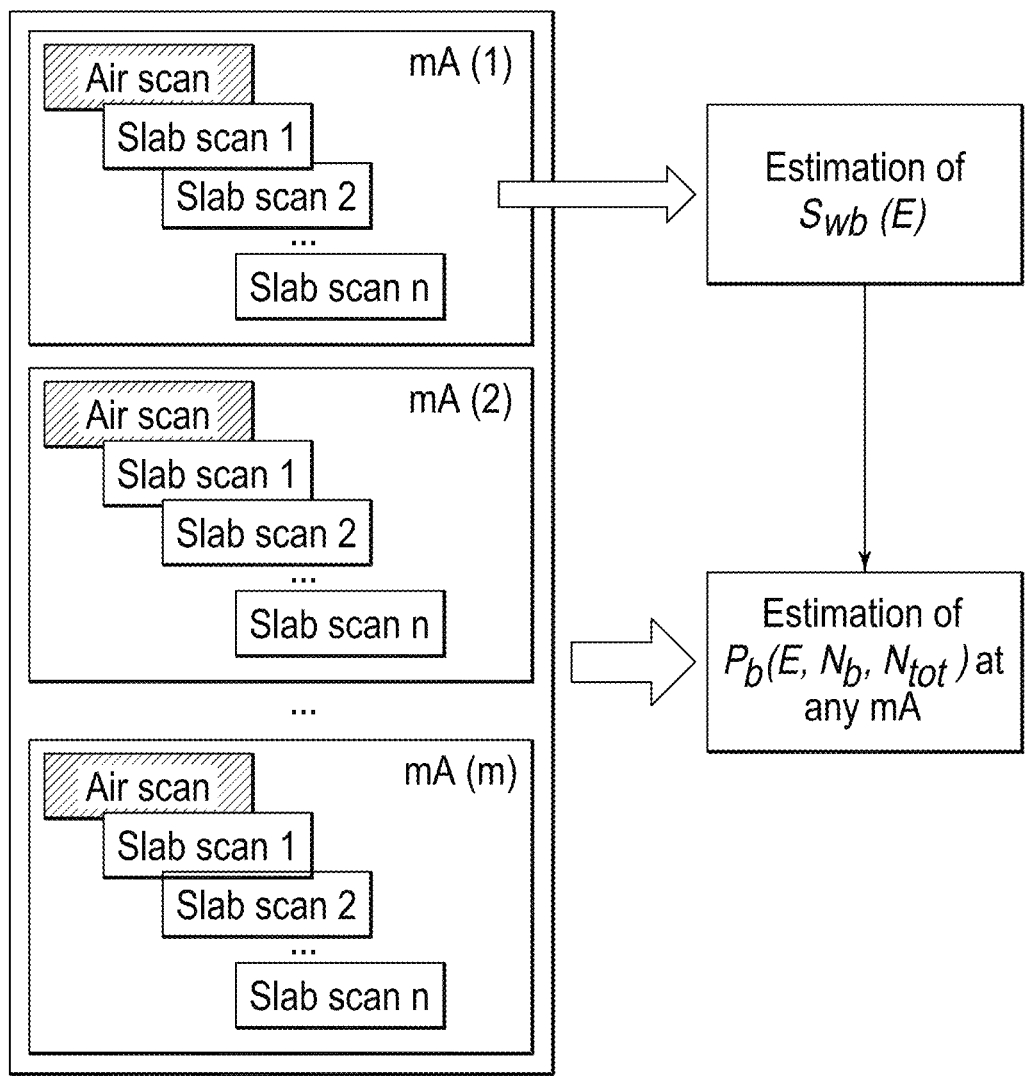
FIG. 5 shows a schematic of another calibration structure design, where a universal pileup correction table $P_b$ is generated for the entire mA range.

For calibration of the pileup correction term $P_b$ in step 3, the same slab material and path lengths are used for scans at high mA settings. The calibration data can be grouped for each mA and generate different correction tables for each mA setting (FIG. 4), or include measurements at all flux ranges (e.g., from low to high mA, from high to low mA, or with most frequently used values first) to generate a universal correction table for a continuous mA setting (FIG. 5).

The calibration measurements should be taken with sufficient statistics to minimize the influence of the statistical fluctuation. One non-limiting example is to use >1000 times more statistics as the typical integration period for the calibration data sets to minimize the transferred statistical error in the calibration. Each energy bin b of the calibration measurements will be used to update the corresponding $S_{wb}(E)$ and $P_b(E, N_b, N_{tot})$.

Since one can only do limited number of measurements with a few energy bins, the estimation is very ill-conditioned. In this case, a good initial guess is crucial for an accurate estimation as it provides additional constraints for the EM method. One of the design variations to accommodate non-ideal detectors is to allow a more flexible energy window for each bin in the initial guess of $S_b$, especially with small variations in the actual energy threshold setting of the ASIC. By setting the low threshold x keV lower, and high threshold y keV higher, the initial $S_b$ becomes:

$$S_b(E) = \int_{E_{bL}-x}^{E_{bH}+y} R(E,E') dE' \qquad (8)$$

where x, y can be chosen between 5 to 10 keV to allow certain variations in the ASIC performance, while still providing additional constraints for the EM problem.

To capture the spectrum variation across the fan beam after bowtie filter and detector response variation across different detector pixels, this calibration process is done pixel by pixel with each bowtie/filter configuration.

The design described in the present application employs more than two materials in the calibration, which provides more sensitivity to constraint the weighted bin response function estimation problem of the photon counting detectors.

In addition, the method utilizes a different parameterization for the high flux pileup correction terms $P_b$ which is now a function of E, $N_b$ and $N_{tot}$. The total count term $N_{tot}$ is introduced for a better approximation of the true pileup phenomena, and can significantly improve the model capability at higher flux condition with fewer parameters.

Furthermore, various calibration path length ranges are used at different fan angles to improve the calibration accuracy and efficiency. The slab scans used for the forward model calibration can be selected based on the imaging task to generate the best image quality.

Finally, a different scheme is presented to calculate an initial guess of the weighted bin response function by enlarging the energy threshold window, to accommodate non-ideal detector/ASIC performance.

Numerous modifications and variations of the embodiments presented herein are possible in light of the above teachings. It is therefore to be understood that within the scope of the claims, the disclosure may be practiced otherwise than as specifically described herein.

The invention claimed is:

1. A method for calibrating a response of a photon counting detector (PCD) for material decomposition in a photon counting computed tomography (CT) system, the method comprising:
   (1) at each pixel of the PCD, performing a plurality of low flux scans comprising phantom scans to obtain counts for each of a plurality of energy bins;
   (2) estimating first parameters, which are dependent on energy, based on the counts;
   (3) estimating second parameters which are dependent on total counts of all energy bins, based on the first parameters; and
   (4) performing a material decomposition in object/patient scans to estimate the basis material based on the first parameters and the second parameters.

2. The method according to the claim 1, wherein,
the estimating the first parameters, based on the counts, is performed using expectation maximization (EM).

3. The method according to claim 1, wherein,
the low flux scans are defined as occurring when nτ<x, where x ~0.005-0.01, n is the pixel count rate, and τ is the effective dead time of the PCD Application Specific Integrated Circuit (ASIC).

4. The method according to the claim 1, wherein,
slabs used in the phantom scans include polypropylene, water, aluminium, titanium/copper, and k-edge materials.

5. The method according to the claim 2, wherein
an initial guess of the first parameters is based on detector response function and low and high energy threshold of each counting bin, respectively.

6. The method according to claim 1, wherein
calibration is performed pixel by pixel.

7. The method according to claim 1, wherein
the first parameters depend on a bin response function.

8. The method according to claim 1, wherein
the second parameters are related to pileup correction terms.

9. A method for calibrating a response of a photon counting detector (PCD) for material decomposition in a photon counting computed tomography (CT) system, the method comprising:
   (1) at each pixel, performing a plurality of low flux scans comprising phantom scans to obtain counts for each energy bin;
   (2) estimating first parameters, which are dependent on energy, based on the counts;
   (3) repeating (1) for different current intensities and at a same tube voltage and using same phantoms, to obtain a universal table of estimated second parameters which are dependent to total counts of all energy bins based on the first parameters, in an entire current intensity range; and
   (4) performing a material decomposition in object/patient scans to estimate basis material based on the first and the second parameters.

10. The method according to claim 9, wherein
the estimating the first parameters, based on the counts, is performed using expectation maximization (EM).

11. The method according to claim 9, wherein
the low flux scans are defined as occurring when nτ<x, where x ~0.005-0.01 and n is the pixel count rate, and τ is the effective dead time of the PCD Application Specific Integrated Circuit (ASIC).

12. The method according to claim 9, wherein
slabs used in the phantom scans include polypropylene, water, aluminium, titanium/copper, and k-edge materials.

13. The method according to claim 10, wherein
an initial guess of the first parameters is based on detector response function, and low and high energy threshold of each counting bin, respectively.

14. The method according to claim 9, wherein
the first parameters depend on a bin response function.

15. The method according to claim 9, wherein
the second parameters are related to pileup correction terms.

* * * * *